United States Patent [19]
Lok et al.

[11] Patent Number: 5,965,704
[45] Date of Patent: Oct. 12, 1999

[54] CLASS TWO CYTOKINE RECEPTOR-11

[75] Inventors: Si Lok, Seattle; Robyn L Adams, Bellevue; Anna C. Jelmberg, Issaquah; Theodore E. Whitmore, Redmond; Theresa M. Farrah, Seattle, all of Wash.

[73] Assignee: ZymoGenetics, Inc., Seattle, Wash.

[21] Appl. No.: 08/906,713

[22] Filed: Aug. 5, 1997

[51] Int. Cl.⁶ .................................................. C07K 14/715
[52] U.S. Cl. ......................... 530/350; 530/300; 530/351; 536/23.1; 536/23.5
[58] Field of Search .................................... 530/300, 350, 530/351; 536/23.1, 23.5

[56] References Cited

U.S. PATENT DOCUMENTS 5,789,192  8/1998  Moore et al. ........................... 435/69.1

FOREIGN PATENT DOCUMENTS

94/13801  6/1994  WIPO .

OTHER PUBLICATIONS

Liu et al., *Journal of Immunology* 152:1821–1829, 1994.
Hillier et al., The Wash U–Merck EST Project, Feb. 23, 1995, GenBank Acc. No.:T70354.
Hillier et al., The Wash U–Merck EST Project, Feb. 23, 1995, GenBank Acc. No.:T70439.
Hillier et al., GenBank Accession No.:AA132964, Nov. 27, 1996.
Hillier et al., GenBank Accession No.:T70439, Feb. 23, 1995.
Henikoff et al., Amino acid substitution matrices from protein blocks, Proc. Natl. Acad. Sci., USA, 89:10915–10919, Nov. 1992.
Stites et al., eds., Basic and Clinical Immunology, Appleton & Lange: Norwalk, CT, p. 53, 1994.

*Primary Examiner*—Lila Feisee
*Assistant Examiner*—Claire M. Kaufman
*Attorney, Agent, or Firm*—Paul G. Lunn, Esq.

[57] ABSTRACT

Novel class II cytokine receptor polypeptides, polynucleotides encoding the polypeptides, an related compositions and methods are disclosed. Th polypeptides comprise an extracellular domain of a cell-surface receptor that is expressed in pancreas, small intestine, colon and thymus. The polypeptides may be used within methods for detecting ligands that promote the proliferation and/or differentiation of these organs.

5 Claims, No Drawings

CLASS TWO CYTOKINE RECEPTOR-11

BACKGROUND OF THE INVENTION

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type II cytokine receptor family (CRF2), based upon a characteristic 200 residue extracellular domain. The demonstrated in vivo activities of these interferons illustrate the enormous clinical potential of, and need for, other cytokines, cytokine agonists, and cytokine antagonists.

SUMMARY OF THE INVENTION

The present invention fills this need by providing novel cytokine receptors and related compositions and methods. In particular, the present invention provides for an extracellular ligand-binding region of a mammalian Zcytor11 receptor, alternatively also containing either a transmembrane domain or both an intracellular domain and a transmembrane domain.

Within one aspect, the present invention provides an isolated polynucleotide encoding a ligand-binding receptor polypeptide. The polypeptide comprises a sequence of amino acids selected from the group consisting of (a) residues 18 to 228 of SEQ ID NO:2; (b) allelic variants of (a); and (c) sequences that are at least 80% identical to (a) or (b). Within one embodiment, the polypeptide comprises residues 18 to 228 of SEQ ID NO:2. Within another embodiment, the polypeptide encoded by the isolated polynucleotide further comprises a transmembrane domain. The transmembrane domain may comprise residues 229 to 251 of SEQ ID NO:2, or an allelic variant thereof. Within another embodiment, the polypeptide encoded by the isolated polynucleotide further comprises an intracellular domain, such as an intracellular domain comprising residues 252 to 574 of SEQ ID NO:2, or an allelic variant thereof. Within further embodiments, the polynucleotide encodes a polypeptide that comprises residues 1 to 574, 1 to 251, 1 to 228, 18 to 251 or 18 to 574 of SEQ ID NO:2. Within an additional embodiment, the polypeptide further comprises an affinity tag. Within a further embodiment, the polynucleotide is DNA.

Within a second aspect of the invention there is provided an expression vector comprising (a) a transcription promoter; (b) a DNA segment encoding a ligand-binding receptor polypeptide, wherein the ligand-binding receptor polypeptide comprises a sequence of amino acids selected from the group consisting of: (i) residues 18–228 or any one of the residues described above of SEQ ID NO:2; (ii) allelic variants of (i); and (iii) sequences that are at least 80% identical to (i) or (ii); and (c) a transcription terminator, wherein the promoter, DNA segment, and terminator are operably linked. The ligand-binding receptor polypeptide may further comprise a secretory peptide, a transmembrane domain, a transmembrane domain and an intracellular domain, or a secretory peptide, a transmembrane domain and an intracellular domain.

Within a third aspect of the invention there is provided a cultured eukaryotic cell into which has been introduced an expression vector as disclosed above, wherein said cell expresses a receptor polypeptide encoded by the DNA segment. Within one embodiment, the cell further expresses a necessary receptor subunit which forms a functional receptor complex. Within another embodiment, the cell is dependent upon an exogenously supplied hematopoietic growth factor for proliferation.

Within a fourth aspect of the invention there is provided an isolated polypeptide comprising a segment selected from the group consisting of (a) residues 18 to 228 of SEQ ID NO:2; (b) allelic variants of (a); and (c) sequences that are at least 80% identical to (a) or (b), wherein said polypeptide is substantially free of transmembrane and intracellular domains ordinarily associated with hematopoietic receptors. Additional polypeptides of the present invention include Within one embodiment, the polypeptide comprises residues 18 to 228 of SEQ ID NO:2. Within another embodiment, the polypeptide further comprises a transmembrane domain. The transmembrane domain may comprise residues 229 to 251 of SEQ ID NO:2, or an allelic variant thereof. Within another embodiment, the polypeptide further comprises an intracellular domain, such as an intracellular domain comprising residues 252 to 574 of SEQ ID NO:2, or an allelic variant thereof. Within further embodiments the polypeptide that comprises residues 1 to 574, 1 to 251, 1 to 228, 18 to 251 or 18 to 574 of SEQ ID NO:2.

Within one embodiment, the polypeptide further comprises an immunoglobulin $F_C$ polypeptide. Within a another embodiment, the polypeptide further comprises an affinity tag, such as polyhistidine, protein A, glutathione S transferase, or an immunoglobulin heavy chain constant region.

Within a further aspect of the invention there is provided a chimeric polypeptide consisting essentially of a first portion and a second portion joined by a peptide bond. The first portion of the chimeric polypeptide consists essentially of a ligand binding domain of a receptor polypeptide selected from the group consisting of (a) a receptor polypeptide as shown in SEQ ID NO:2; (b) allelic variants of SEQ ID NO:2; and (c) receptor polypeptides that are at least 80% identical to (a) or (b). The second portion of the chimeric polypeptide consists essentially of an affinity tag. Within one embodiment the affinity tag is an immunoglobulin $F_C$ polypeptide. The invention also provides expression vectors encoding the chimeric polypeptides and host cells transfected to produce the chimeric polypeptides.

The present invention also provides for an isolated polynucleotide encoding a polypeptide selected from a group defined SEQ ID NO:2 consisting of residues 1 to 228, residues 1 to 251, residues 1 to 574, residues 2 to 228, residues 2 to 251 and residues 2 to 574. Also claimed are the isolated polypeptide expressed by these polynucleotides.

The invention also provides a method for detecting a ligand within a test sample, comprising contacting a test sample with a polypeptide as disclosed above, and detecting binding of the polypeptide to ligand in the sample. Within one embodiment the polypeptide further comprises transmembrane and intracellular domains. The polypeptide can be membrane bound within a cultured cell, wherein the detecting step comprises measuring a biological response in the cultured cell. Within another embodiment, the polypeptide is immobilized on a solid support.

Within an additional aspect of the invention there is provided an antibody that specifically binds to a polypeptide as disclosed above, as well as an anti-idiotypic antibody which binds to the antigen-binding region of an antibody to Zcytor11.

In still another aspect of the present invention, polynucleotide primers and probes are provided which can detect mutations in the Zcytor11 gene. The polynucleotide probe should at least be 20–25 bases in length, preferably at least 50 bases in length and most preferably about 80 to 100 bases in length. In addition to the detection of mutations, these probes can be used to discover the Zcytor11 gene in other mammalian species. The probes can either be positive strand or anti-sense strands, and they can be comprised of DNA or RNA.

These and other aspects of the invention will become evident upon reference to the following detailed description and the attached drawing.

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

Analysis of the tissue distribution of the mRNA corresponding to this novel DNA showed that mRNA level was highest in pancreas, followed by a much lower levels in thymus, colon and small intestine. The receptor has been designated "Zcytor11".

Cytokine receptors subunits are characterized by a multi-domain structure comprising a ligand-binding domain and an effector domain that is typically involved in signal transduction. Multimeric cytokine receptors include homodimers (e.g., PDGF receptor $\alpha\alpha$ and $\beta\beta$ isoforms, erythropoietin receptor, MPL [thrombopoietin receptor], and G-CSF receptor), heterodimers whose subunits each have ligand-binding and effector domains (e.g., PDGF receptor $\alpha\beta$ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif. Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, Ann. Reports Med. Chem. 26:221–228, 1991 and Cosman, Cytokine 5:95–106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Cell-surface cytokine receptors are further characterized by the presence of additional domains. These receptors are anchored in the cell membrane by a transmembrane domain characterized by a sequence of hydrophobic amino acid residues (typically about 21–25 residues), which is commonly flanked by positively charged residues (Lys or Arg). On the opposite end of the protein from the extracellular domain and separated from it by the transmembrane domain is an intracellular domain.

The novel receptor of the present invention, Zcytor11, is a class II cytokine receptor. These receptors usually bind to four-helix-bundle cytokines. Interleukin-10 and the interferons have receptors in this class (e.g., interferon-gamma alpha and beta chains and the interferon-alpha/beta receptor alpha and beta chains). Class II cytokine receptors are characterized by the presence of one or more cytokine receptor modules (CRM) in their extracellular domains. The CRMs of class II cytokine receptors are somewhat different than the better known CRMs of class I cytokine receptors. While the class II CRMs contain two type-III fibronectin-like domains, they differ in organization.

Zcytor11, like all known class II receptors except interferon-alpha/beta receptor alpha chain, has only a single class II CRM in its extracellular domain. Zcytor11 appears to be a receptor for a helical cytokine of the interferon/IL-10 class. Using the Zcytor11 receptor we can identify ligands and additional compounds which would be of significant therapeutic value.

As was stated above, Zcytor11 is similar to the interferon α receptor α chain. Uze et al. *Cell* 60 255–264 (1996) Analysis of a human cDNA clone encoding Zcytor11 (SEQ ID NO:1) revealed an open reading frame encoding 574 amino acids (SEQ ID NO:2) comprising an extracellular ligand-binding domain of approximately 211 amino acid residues (residues 18–228 of SEQ ID NO:2), a transmembrane domain of approximately 23 amino acid residues (residues 229–251 of SEQ ID NO:2), and an intracellular domain of approximately 313 amino acid residues (residues 252 to 574 of SEQ ID NO:2). Those skilled in the art will recognize that these domain boundaries are approximate and are based on alignments with known proteins and predictions of protein folding. Deletion of residues from the ends of the domains is possible.

Within preferred embodiments of the invention the isolated polynucleotides will hybridize to similar sized regions of SEQ ID NO:1 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from pancreas or prostate tissues although cDNA can also be prepared using RNA from other tissues or isolated as genomic DNA. Total RNA can be prepared using guanidine HCl extraction followed by isolation by centrifugation in a CsCl gradient [Chirgwin et al., *Biochemistry* 18:52–94, (1979)]. Poly $(A)^+$ RNA is prepared from total RNA using the method of Aviv and Leder *Proc. Natl. Acad. Sci. USA* 69:1408–1412, (1972). Complementary DNA (cDNA) is prepared from poly$(A)^+$ RNA using known methods. Polynucleotides encoding Zcytor11 polypeptides are then identified and isolated by, for example, hybridization or PCR.

Those skilled in the art will recognize that the sequences disclosed in SEQ ID NOS:1 and 2 represent single alleles of the human Zcytor11 receptor. Allelic variants of these sequences can be cloned by probing cDNA or genomic libraries from different individuals according to standard procedures.

The present invention further provides counterpart receptors and polynucleotides from other species ("species orthologs"). Of particular interest are Zcytor11 receptors from other mammalian species, including murine, porcine, ovine, bovine, canine, feline, equine, and non-human primates. Species orthologs of the human Zcytor11 receptor can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial cDNA of human and other primates or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones.

The present invention also provides isolated receptor polypeptides that are substantially homologous to the receptor polypeptide of SEQ ID NO: 2. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO:2. Such polypeptides will more preferably be at least 90% identical, and most preferably 95% or more identical to SEQ ID NO:2. Percent sequence identity is determined by conventional methods. See, for example, Altschul et al., *Bull. Math. Bio.* 48: 603–616, (1986) and Henikoff and Henikoff, *Proc. Natl. Acad. Sci. USA* 89:10915–10919, (1992). Briefly, two amino acid sequences are aligned to optimize the alignment scores using a gap opening penalty of 10, a gap extension penalty of 1, and the "BLOSUM 62" scoring matrix of Henikoff and Henikoff (id.) as shown in Table 2 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 3) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A [Nilsson et al., EMBO J. 4:1075, (1985); Nilsson et al., Methods Enzymol. 198:3, (1991)], glutathione S transferase [Smith and Johnson, Gene 67:31, 1988), or other antigenic epitope or binding domain. See, in general Ford et al., Protein Expression and Purification 2: 95–107, (1991. DNAs encoding affinity tags are available from commercial suppliers (e.g., Pharmacia Biotech, Piscataway, N.J.).

TABLE 3

Conservative amino acid substitutions

| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the receptor polypeptides of the present invention can be identified according to procedures known in the art, such as site-directed mutagenesis or alanine-scanning mutagenesis [Cunningham and Wells, Science 244, 1081–1085, (1989); Bass et al., Proc. Natl. Acad. Sci. USA 88:4498–4502, (1991)]. In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., Science 255:306–312, (1992); Smith et al., J. Mol. Biol. 224:899–904, (1992); Wlodaver et al., FEBS Lett. 309:59–64, (1992)]. The identities of essential amino acids can also be inferred from analysis of homologies with related receptors.

Multiple amino acid substitutions can be made and tested using known methods of mutagenesis and screening, such as those disclosed by Reidhaar-Olson and Sauer Science 241:53–57, (1988) or Bowie and Sauer Proc. Natl. Acad. Sci. USA 86:2152–2156, (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display e.g., Lowman et al., Biochem. 30:10832–10837, (1991); Ladner et al., U.S. Pat. No. 5,223,409; Huse, WIPO Publication WO 92/06204) and region-directed mutagenesis [Derbyshire et al., Gene 46:145, (1986); Ner et al., DNA 7:127, (1988)].

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 18 to 228 of SEQ ID NO:2 or allelic variants thereof and retain the ligand-binding properties of the wild-type receptor. Such polypeptides may include additional amino acids from an extracellular ligand-binding domain of a Zcytor11 receptor as well as part or all of the transmembrane and intracellular domains. Such polypeptides may also include additional polypeptide segments as generally disclosed above.

The receptor polypeptides of the present invention, including full-length receptors, receptor fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., (1989), and Ausubel et al., ibid., which are incorporated herein by reference.

In general, a DNA sequence encoding a Zcytor11 receptor polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcytor11 receptor polypeptide into the secretory pathway of a host cell, a secretory signal sequence (also known as a leader sequence, prepro sequence or pre sequence) is provided in the expression vector. The secretory signal sequence may be that of the receptor, or may be derived from another secreted protein (e.g., t-PA) or synthesized de novo. The secretory signal sequence is joined to the Zcytor11 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection [Wigler et al., *Cell* 14:725, (1978); Corsaro and Pearson, *Somatic Cell Genetics* 7:603, (1981): Graham and Van der Eb, *Virology* 52:456, (1973)], electroporation [Neumann et al., *EMBO J.* 1:841–845, (1982)], DEAE-dextran mediated transfection [Ausubel et al., eds., *Current Protocols in Molecular Biology,* (John Wiley and Sons, Inc., N.Y., 1987), and liposome-mediated transfection (Hawley-Nelson et al., *Focus* 15:73, (1993); Ciccarone et al., *Focus* 15:80, (1993)], which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al.,*J. Gen. Virol.* 36:59–72, 1977) and Chinese hamster ovary (e.g. CHO-K1; ATCC No. CCL61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci. (Bangalore)* 11:47–58, (1987).

Fungal cells, including yeast cells, and particularly cells of the genus Saccharomyces, can also be used within the present invention, such as for producing receptor fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, (1986) and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Within one aspect of the present invention, a novel receptor is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing Zcytor11 receptors and transducing a receptor-mediated signal include cells that express other receptor subunits which may form a functional complex with Zcytor11. These subunits may include those of the interferon receptor family or of other class II or class I cytokine receptors. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 [Palacios and Steinmetz, *Cell* 41: 727–734, (1985)] which is an IL-3 dependent murine pre-B cell line. Other cell lines include BHK, COS-1 and CHO cells.

Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon a Zcytor11 ligand.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by calorimetric assay based on the metabolic breakdown of 3-(4,5-dimethylthiazol-2-yl)-2,5-diphenyl tetrazolium bromide (MTT) [Mosman, *J. Immunol. Meth.* 65: 55–63, (1983)]. An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563–572, (1989). A preferred such reporter gene is a luciferase gene [de Wet et al., *Mol. Cell. Biol.* 7:725, (1987)]. Expression of the luciferase gene is detected by luminescence using methods known in the art [e.g., Baumgartner et al., *J. Biol. Chem.* 269:29094–29101, (1994); Schenborn and Goiffin, *Promega_Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

A natural ligand for the Zcytor11 receptor can also be identified by mutagenizing a cell line expressing the receptor and culturing it under conditions that select for autocrine growth. See WIPO publication WO 95/21930. Within a typical procedure, IL-3 dependent BaF3 cells expressing Zcytor11 and the necessary additional subunits are mutagenized, such as with 2-ethylmethanesulfonate (EMS). The cells are then allowed to recover in the presence of IL-3, then transferred to a culture medium lacking IL-3 and IL-4. Surviving cells are screened for the production of a Zcytor11 ligand, such as by adding soluble receptor to the culture medium or by assaying conditioned media on wild-type BaF3 cells and BaF3 cells expressing the receptor.

An additional screening approach provided by the present invention includes the use of hybrid receptor polypeptides. These hybrid polypeptides fall into two general classes. Within the first class, the intracellular domain of Zcytor11, comprising approximately residues 252 to 574 of SEQ ID NO:2, is joined to the ligand-binding domain of a second receptor. It is preferred that the second receptor be a hematopoietic cytokine receptor, such as mpl receptor [Souyri et al., *Cell* 63: 1137–1147, (1990)]. The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by Zcytor11 while using readily available ligands. This system can also be used to determine if particular cell lines are capable of responding to signals transduced by Zcytor11. A second class of hybrid receptor polypeptides comprise the extracellular (ligand-binding)

domain of Zcytor11 (approximately residues 18 to 228 of SEQ ID NO:2) with an intracellular domain of a second receptor, preferably a hematopoietic cytokine receptor, and a transmembrane domain. Hybrid receptors of this second class are expressed in cells known to be capable of responding to signals transduced by the second receptor. Together, these two classes of hybrid receptors enable the identification of a responsive cell type for the development of an assay for detecting a Zcytor11 ligand.

Cells found to express the ligand are then used to prepare a cDNA library from which the ligand-encoding cDNA can be isolated as disclosed above. The present invention thus provides, in addition to novel receptor polypeptides, methods for cloning polypeptide ligands for the receptors.

The tissue specificity of Zcytor11 expression suggests a role in the development of the pancreas, small intestine, colon and the thymus. In view of the tissue specificity observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists or antagonist may be useful in specifically regulating the growth and/or development of pancreatic, gasto-intestinal or thymic-derived cells in culture. These compounds are useful as research reagents for characterizing sites of ligand-receptor interaction. In vivo, receptor agonists or antagonists may find application in the treatment pancreatic, gastrointestinal or thymic diseases.

Agonists or antagonists to Zcytor11 may include small families of peptides. These peptides may be identified employing affinity selection conditions that are known in the art, from a population of candidates present in a peptide library. Peptide libraries include combinatory libraries chemically synthesized and presented on solid support [Lam et al., Nature 354: 82–84 (1991)] or are in solution [Houghten et al., BioTechniques 13: 412–421, (1992)], expressed then linked to plasmid DNA [Cull et al., Proc. Natl. Acad. Sci. USA 89: 1865–1869 (1992)] or expressed and subsequently displayed on the surfaces of viruses or cells [Boder and Wittrup, Nature Biotechnology 15: 553–557(1997); Cwirla et al. Science 276: 1696–1699 (1997)].

Zcytor11 may also be used within diagnostic systems for the detection of circulating levels of ligand. Within a related embodiment, antibodies or other agents that specifically bind to Zcytor11 can be used to detect circulating receptor polypeptides. Elevated or depressed levels of ligand or receptor polypeptides may be indicative of pathological conditions, including cancer.

Zcytor11 receptor polypeptides can be prepared by expressing a truncated DNA encoding the extracellular domain, for example, a polypeptide which contains residues 18 through 228 of a human Zcytor11 receptor (SEQ ID NO:2 or the corresponding region of a non-human receptor. It is preferred that the extracellular domain polypeptides be prepared in a form substantially free of transmembrane and intracellular polypeptide segments. For example, the C-terminus of the receptor polypeptide may be at residue 228 of SEQ ID NO:2 or the corresponding region of an allelic variant or a non-human receptor. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide [Hopp et al., Biotechnology 6:1204–1210, (1988); available from Eastman Kodak Co., New Haven, Conn.] or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_C$ fragment, which contains two constant region domains and a hinge region but lacks the variable region. Such fusions are typically secreted as multimeric molecules wherein the $F_C$ portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a Zcytor11-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate gastrointestinal, pancreatic or thymic functions. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_C$ region and used in an ELISA format.

A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, J. Immunol. Methods 145:229–240, (1991) and Cunningham and Wells, J. Mol. Biol. 234:554–563, (1993). A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity. See, Scatchard, Ann. NY Acad. Sci. 51: 660–672, (1949) and calorimetric assays [Cunningham et al., Science 253:545–548, (1991); Cunningham et al., Science 254:821–825, (1991)].

A receptor ligand-binding polypeptide can also be used for purification of ligand. The receptor polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

Zcytor11 polypeptides can also be used to prepare antibodies that specifically bind to Zcytor11 polypeptides. As used herein, the term "antibodies" includes polyclonal antibodies, monoclonal antibodies, single-chain antibodies and antigen-binding fragments thereof such as F(ab')$_2$ and Fab fragments, and the like, including genetically engineered antibodies. Antibodies are defined to be specifically binding if they bind to a Zcytor11 polypeptide with a $K_a$ of greater than or equal to $10^7$/M. The affinity of a monoclonal antibody can be readily determined by one of ordinary skill in the art (see, for example, Scatchard, ibid.).

Methods for preparing polyclonal and monoclonal antibodies are well known in the art. See for example, Sambrook et al., *Molecular Cloning: A Laboratory Manual, Second Edition*, Cold Spring Harbor, N.Y., (1989); and Hurrell, J. G. R., Ed., *Monoclonal Hybridoma Antibodies: Techniques and Applications*, CRC Press, Inc., Boca Raton, Fla., (1982), which are incorporated herein by reference. As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zcytor11 polypeptide may be increased through the use of an adjuvant such as Freund's complete or incomplete adjuvant. A variety of assays known to those skilled in the art can be utilized to detect antibodies which specifically bind to Zcytor11 polypeptides. Exemplary assays are described in detail in *Antibodies: A Laboratory Manual*, Harlow and Lane (Eds.), Cold Spring Harbor Laboratory Press, (1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Antibodies to Zcytor11 may be used for tagging cells that express the receptor, for affinity purification, within diagnostic assays for determining circulating levels of soluble receptor polypeptides, and as antagonists to block ligand binding and signal transduction in vitro and in vivo.

Anti-idiotypic antibodies which bind to the antigenic binding site of antibodies to Zcytor11 are also considered part of the present invention. The antigenic binding region of the anti-idiotypic antibody thus will mimic the ligand binding region of Zcytor11. An anti-idiotypic antibody thus could be used to screen for possible ligands of the Zcytor11 receptor. Thus neutralizing antibodies to Zcytor11 can be used to produce anti-idiotypic antibodies by methods well known in the art as is described in, for example, Sambrook et al., *Molecular Cloning: A Laboratory Manual, Second Edition*, (Cold Spring Harbor, N.Y., 1989); and Hurrell, J. G. R., Ed., *Monoclonal Hybridoma Antibodies: Techniques and Applications*, (CRC Press, Inc., Boca Raton, Fla., 1982).

Zcytor11 maps 84.62 cR from the top of the human chromosome a linkage group on the WICGR radiation hybrid map. The use of surrounding markers positioned Zcytor11 in the 1p35.2 to 35.1 region.

Thus Zcytor11 could be used to generate a probe that could allow detection of an aberration of the Zcytor11 gene in the 1p chromosome which may indicate the presence of a cancerous cells or a predisposition to cancerous cell development. This region of chromosome 1 is frequently involved in visible deletions or loss of heterozygosity in tumors derived from the neural crest cells particularly neuroblastomas and melanomas. For further discussions on developing polynucleotide probes and hybridization see *Current Protocols in Molecular Biology* Ausubel, F. et al. Eds. (John Wiley & Sons Inc. 1991).

The invention is further illustrated by the following non-limiting examples.

EXAMPLE 1

Production a Pancreatic Islet Cell cDNA Library

Zcytor11 was cloned from a pancreatic islet cell cDNA library produced according to the following procedure. RNA extracted from pancreatic islet cells was reversed transcribed in the following manner. The first strand cDNA reaction contained 10 μl of human pancreatic islet cell poly d(T)-selected poly (A)$^+$ mRNA (Clontech, Palo Alto, Calif.) at a concentration of 1.0 mg/ml, and 2 μl of 20 pmole/μl first strand primer ZC6171 (SEQ ID NO: 6) containing an Xho I restriction site. The mixture was heated at 70° C. for 2.5 minutes and cooled by chilling on ice. First strand cDNA synthesis was initiated by the addition of 8 μl of first strand buffer (5× SUPERSCRIPT® buffer; Life Technologies, Gaithersburg, Md.), 4 μl of 100 mM dithiothreitol, and 3 μl of a deoxynucleotide triphosphate (dNTP) solution containing 10 mM each of dTTP, dATP, dGTP and 5-methyl-dCTP (Pharmacia LKB Biotechnology, Piscataway, N.J.) to the RNA-primer mixture. The reaction mixture was incubated at 40° C. for 2 minutes, followed by the addition of 10 μl of 200 U/μl RNase H-reverse transcriptase (SUPERSCRIPT II®; Life Technologies). The efficiency of the first strand synthesis was analyzed in a parallel reaction by the addition of 10 μCi of $^{32}$P-αdCTP to a 5 μl aliquot from one of the reaction mixtures to label the reaction for analysis. The reactions were incubated at 40° C. for 5 minutes, 45° C. for 50 minutes, then incubated at 50° C. for 10 minutes. Unincorporated $^{32}$P-αdCTP in the labeled reaction was removed by chromatography on a 400 pore size gel filtration column (Clontech Laboratories, Palo Alto, Calif.). The unincorporated nucleotides and primers in the unlabeled first strand reactions were removed by chromatography on 400 pore size gel filtration column (Clontech Laboratories, Palo Alto, Calif.). The length of labeled first strand cDNA was determined by agarose gel electrophoresis.

The second strand reaction contained 102 μl of the unlabeled first strand cDNA, 30 μl of 5× polymerase I buffer (125 mM Tris: HCl, pH 7.5, 500 mM KCl, 25 mM MgCl$_2$, 50 mM (NH$_4$)$_2$SO$_4$)), 2.0 μl of 100 mM dithiothreitol, 3.0 μl of a solution containing 10 mM of each deoxynucleotide triphosphate, 7 μl of 5 mM β-NAD, 2.0 μl of 10 U/μl *E. coli* DNA ligase (New England Biolabs; Beverly, Mass.), 5 μl of 10 U/μl *E. coli* DNA polymerase I (New England Biolabs, Beverly, Mass.), and 1.5 μl of 2 U/μl RNase H (Life Technologies, Gaithersburg, Md.). A 10 μl aliquot from one of the second strand synthesis reactions was labeled by the addition of 10 μCi $^{32}$P-αdCTP to monitor the efficiency of second strand synthesis. The reactions were incubated at 16° C. for two hours, followed by the addition of 1 μl of a 10 mM dNTP solution and 6.0 μl T4 DNA polymerase (10 U/μl, Boehringer Mannheim, Indianapolis, Ind.) and incubated for an additional 10 minutes at 16° C. Unincorporated $^{32}$P-αdCTP in the labeled reaction was removed by chromatography through a 400 pore size gel filtration column (Clontech Laboratories, Palo Alto, Calif.) before analysis by agarose gel electrophoresis. The reaction was terminated by the addition of 10.0 μl 0.5 M EDTA and extraction with phenol/chloroform and chloroform followed by ethanol precipitation in the presence of 3.0 M Na acetate and 2 μl of Pellet Paint carrier (Novagen, Madison, Wis.). The yield of cDNA was estimated to be approximately 2 μg from starting mRNA template of 10 μg.

Eco RI adapters were ligated onto the 5' ends of the cDNA described above to enable cloning into an expression vector. A 12.5 μl aliquot of cDNA (~2.0 μg) and 3 μl of 69 pmole/μl of Eco RI adapter (Pharmacia LKB Biotechnology Inc., Piscataway, N.J.) were mixed with 2.5 μl 10× ligase buffer (660 mM Tris-HCl pH 7.5, 100 mM $MgCl_2$), 2.5 μl of 10 mM ATP, 3.5 μl 0.1 M DTT and 1 μl of 15 U/μl T4 DNA ligase (Promega Corp., Madison, Wis.). The reaction was incubated 1 hour at 5° C., 2 hours at 7.5° C., 2 hours at 10° C., 2 hours at 12.5° C. and 16 hours at 10° C. The reaction was terminated by the addition of 65 μl $H_2O$ and 10 μl 10× H buffer (Boehringer Mannheim, Indianapolis, Ind.) and incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced. Restriction enzyme digestion was carried out in a reaction mixture by the addition of 1.0 μl of 40 U/μl Xho I (Boehringer Mannheim, Indianapolis, Ind.). Digestion was carried out at 37° C. for 45 minutes. The reaction was terminated by incubation at 70° C. for 20 minutes and chromatography through a 400 pore size gel filtration column (Clontech Laboratories, Palo Alto, Calif.).

The cDNA was ethanol precipitated, washed with 70% ethanol, air dried and resuspended in 10.0 μl water, 2 μl of 10× kinase buffer (660 mM Tris-HCl, pH 7.5, 100 mM $MgCl_2$), 0.5 μl 0.1 M DTT, 2 μl 10 mM ATP, 2 μl T4 polynucleotide kinase (10 U/μl, Life Technologies, Gaithersburg, Md.). Following incubation at 37° C. for 30 minutes, the cDNA was ethanol precipitated in the presence of 2.5 M Ammonium Acetate, and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10× β-agarose I buffer (New England Biolabs) was added to the tube, and the agarose was melted by heating to 65° C. for 15 minutes. Following equilibration of the sample to 45° C., 3 μl of 1 U/μl β-agarose I (New England Biolabs, Beverly, Mass.) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 40 μl water.

Following recovery from low-melt agarose gel, the cDNA was cloned into the Eco RI and Xho I sites of pBLUE-SCRIPT SK+ vector (Gibco/BRL, Gaithersburg, Md.) and electroporated into DH10B cells. Bacterial colonies containing ESTs of known genes were identified and eliminated from sequence analysis by reiterative cycles of probe hybridization to hi-density colony filter arrays (Genome Systems, St. Louis, Mich.). cDNAs of known genes were pooled in groups of 50–100 inserts and were labeled with $^{32}$P-αdCTP using a MEGAPRIME labeling kit (Amersham, Arlington Heights, Ill.). Colonies which did not hybridize to the probe mixture were selected for sequencing. Sequencing was done using an ABI 377 sequencer using either the T3 or the reverse primer. The resulting data were analyzed which resulted in the identification of EST LISF104376 (SEQ ID NO: 3).

EXAMPLE 2.

Cloning of Zcytor11

Expressed sequence tag (EST) LISF104376 (SEQ ID NO:3) contained in plasmid pSLIS4376 was isolated from a human pancreatic islet cell cDNA library. Following sequencing of the entire pSLIS4376 cDNA insert, it was determined not to encode a full-length Zcytor11 polypeptide.

A full length Zcytor11 encoding cDNA was isolated by screening a human islet cDNA library using a probe that was generated by PCR primers ZC14,295 (SEQ ID NO:4) and ZC14294 (SEQ ID NO:5) and the pSLIS4376 template. (For details on the construction of the pancreatic islet cell cDNA library, see Example 2 below.) The resulting probe of 276 bp containing nucleotides 142 to 417 of SEQ ID NO:1 was purified by chromatography through a 100 pore size spin column (Clontech, Palo Alto, Calif.). The purified probe was labeled with $^{32}$P-αCTP using a MEGAPRIME® labeling kit (Amersham Corp., Arlington Heights, Ill.). The labeled probe was purified on a NUCTRAP® purification column (Stratagene Cloning Systems, La Jolla, Calif.) for library screening.

Following recovery of the islet cDNA from a low-melt agarose gel from Example 1, the cDNA was cloned into the Eco RI and Xho I sites; of pBLUESCRIPT SK+ (Gibco/BRL, Gaithersburg, Md.) and electroporated into DH10B cells. Bacterial clones from resulting cDNA library were individually placed on a grid of a high-density colony filter arrays (Genome Systems, St. Louis, Mich.) and were probed with the labeled Zyctor11 probe described above. A glycerol stock of each clone on each grid was also made to expedite the isolation of positive clones. The filters were first prewashed in an aqueous solution containing 0.25× standard sodium citrate (SSC), 0.25% sodium dodecyl sulfate (SDS) and 1 mM EDTA to remove cellular debris and then prehybridized in a hybridization solution (5×SSC, 5× Denhardt's solution, 0.2% SDS and 1 mM EDTA) containing 100 μg/ml heat-denature, sheared salmon sperm DNA).

Fifty nanograms of the PCR-derived Zcytor11 probe was radiolabeled with $^{32}$P-αdCTP by random priming using the MEGAPRIME® (DNA labeling system (Amersham, Arlington Heights, Ill.). The prehybridization solution was replaced with fresh hybridization containing 1×10$^6$ cpm/ml probe and allowed to hybridize at 65° C. overnight. The filters were washed in a wash buffer containing 0.25× SSC, 0.25% SDS and 1 mM EDTA at 65° C.

Following autoradiography, three signals were detected among 40,000 clones on the grids of the filter array. From the grid coordinates of the positive signals, the corresponding clones, pSLR11-1, pSLR11-2 and pSLR11-3 were

EXAMPLE 3

Expression of Human Zcytor11 mRNA in Human Tissues

Poly(A)+ RNAs isolated brain, colon, heart, kidney, liver, lung, ovary, pancreas, prostate, placenta, peripheral blood leukocytes, stomach, spleen, skeletal muscle, small intestine, testis, thymus, thyroid, spinal cord, lymph node, trachea, adrenal gland and bone marrow were hybridized under high stringency conditions with a radiolabeled DNA probe containing nucleotides 181–456 of (SEQ ID NO:1). Membranes were purchased from Clontech. The membrane were washed with 1.0× SSC, 0.1% SDS at 50° C. and autoradiographed for 24 hours. The mRNA levels were highest in pancreas with low levels in colon, small intestine and thymus. The receptor mRNA localization suggests that Zcytor11 may regulate gastrointestinal, pancreatic or thymic functions.

retrieved from the glycerol stock and their inserts sequenced. The insert in pSLR11-1 was determined to be 2831 base pairs (bp) and encoded full-length Zcytor11 polypeptide.

EXAMPLE 4

Chromosomal Assignment and Placement of Zcytor11

Zcytor11 was mapped to chromosome 1 using the commercially available version of the Whitehead Institute/MIT Center for Genome Research's "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

We claim:

1. An isolated polypeptide which comprises an amino acid sequence defined by residues 18–228 of SEQ ID NO: 2.

2. An isolated polypeptide of claim 1 further comprising a sequence which defines a transmembrane domain and a sequence which defines an intracellular domain.

3. An isolated polypeptide according to claim 1 further comprising a sequence which defines an affinity tag.

4. An isolated polypeptide which comprises an amino acid sequence defined by residues 18–574 of SEQ ID NO:2.

5. An isolated polypeptide selected from the group consisting of residues 1 to 228, residues 1 to 251, residues 1 to 574, residues 2 to 228, residues 2 to 551, and residues 2 to 574 of SEQ ID NO: 2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2831 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 34...1755
      (D) OTHER INFORMATION:

(xi) SEQUENCE DESCRIPTION: SEQ ID NO:1:

```
TAGAGGCCAA GGGAGGGCTC TGTGCCAGCC CCG ATG AGG ACG CTG CTG ACC ATC        54
                                    Met Arg Thr Leu Leu Thr Ile
                                     1               5

TTG ACT GTG GGA TCC CTG GCT GCT CAC GCC CCT GAG GAC CCC TCG GAT        102
Leu Thr Val Gly Ser Leu Ala Ala His Ala Pro Glu Asp Pro Ser Asp
        10              15                  20

CTG CTC CAG CAC GTG AAA TTC CAG TCC AGC AAC TTT GAA AAC ATC CTG        150
Leu Leu Gln His Val Lys Phe Gln Ser Ser Asn Phe Glu Asn Ile Leu
    25                  30                  35

ACG TGG GAC AGC GGG CCA GAG GGC ACC CCA GAC ACG GTC TAC AGC ATC        198
Thr Trp Asp Ser Gly Pro Glu Gly Thr Pro Asp Thr Val Tyr Ser Ile
40                  45                  50                  55

GAG TAT AAG ACG TAC GGA GAG AGG GAC TGG GTG GCA AAG AAG GGC TGT        246
Glu Tyr Lys Thr Tyr Gly Glu Arg Asp Trp Val Ala Lys Lys Gly Cys
                60                  65                  70

CAG CGG ATC ACC CGG AAG TCC TGC AAC CTG ACG GTG GAG ACG GGC AAC        294
Gln Arg Ile Thr Arg Lys Ser Cys Asn Leu Thr Val Glu Thr Gly Asn
            75                  80                  85

CTC ACG GAG CTC TAC TAT GCC AGG GTC ACC GCT GTC AGT GCG GGA GGC        342
Leu Thr Glu Leu Tyr Tyr Ala Arg Val Thr Ala Val Ser Ala Gly Gly
        90                  95                  100

CGG TCA GCC ACC AAG ATG ACT GAC AGG TTC AGC TCT CTG CAG CAC ACT        390
```

-continued

```
        Arg Ser Ala Thr Lys Met Thr Asp Arg Phe Ser Ser Leu Gln His Thr
            105                 110                 115

ACC CTC AAG CCA CCT GAT GTG ACC TGT ATC TCC AAA GTG AGA TCG ATT           438
Thr Leu Lys Pro Pro Asp Val Thr Cys Ile Ser Lys Val Arg Ser Ile
120                 125                 130                 135

CAG ATG ATT GTT CAT CCT ACC CCC ACG CCA ATC CGT GCA GGC GAT GGC           486
Gln Met Ile Val His Pro Thr Pro Thr Pro Ile Arg Ala Gly Asp Gly
                140                 145                 150

CAC CGG CTA ACC CTG GAA GAC ATC TTC CAT GAC CTG TTC TAC CAC TTA           534
His Arg Leu Thr Leu Glu Asp Ile Phe His Asp Leu Phe Tyr His Leu
                155                 160                 165

GAG CTC CAG GTC AAC CGC ACC TAC CAA ATG CAC CTT GGA GGG AAG CAG           582
Glu Leu Gln Val Asn Arg Thr Tyr Gln Met His Leu Gly Gly Lys Gln
            170                 175                 180

AGA GAA TAT GAG TTC TTC GGC CTG ACC CCT GAC ACA GAG TTC CTT GGC           630
Arg Glu Tyr Glu Phe Phe Gly Leu Thr Pro Asp Thr Glu Phe Leu Gly
            185                 190                 195

ACC ATC ATG ATT TGC GTT CCC ACC TGG GCC AAG GAG AGT GCC CCC TAC           678
Thr Ile Met Ile Cys Val Pro Thr Trp Ala Lys Glu Ser Ala Pro Tyr
200                 205                 210                 215

ATG TGC CGA GTG AAG ACA CTG CCA GAC CGG ACA TGG ACC TAC TCC TTC           726
Met Cys Arg Val Lys Thr Leu Pro Asp Arg Thr Trp Thr Tyr Ser Phe
                220                 225                 230

TCC GGA GCC TTC CTG TTC TCC ATG GGC TTC CTC GTC GCA GTA CTC TGC           774
Ser Gly Ala Phe Leu Phe Ser Met Gly Phe Leu Val Ala Val Leu Cys
                235                 240                 245

TAC CTG AGC TAC AGA TAT GTC ACC AAG CCG CCT GCA CCT CCC AAC TCC           822
Tyr Leu Ser Tyr Arg Tyr Val Thr Lys Pro Pro Ala Pro Pro Asn Ser
            250                 255                 260

CTG AAC GTC CAG CGA GTC CTG ACT TTC CAG CCG CTG CGC TTC ATC CAG           870
Leu Asn Val Gln Arg Val Leu Thr Phe Gln Pro Leu Arg Phe Ile Gln
265                 270                 275

GAG CAC GTC CTG ATC CCT GTC TTT GAC CTC AGC GGC CCC AGC AGT CTG           918
Glu His Val Leu Ile Pro Val Phe Asp Leu Ser Gly Pro Ser Ser Leu
280                 285                 290                 295

GCC CAG CCT GTC CAG TAC TCC CAG ATC AGG GTG TCT GGA CCC AGG GAG           966
Ala Gln Pro Val Gln Tyr Ser Gln Ile Arg Val Ser Gly Pro Arg Glu
                300                 305                 310

CCC GCA GGA GCT CCA CAG CGG CAT AGC CTG TCC GAG ATC ACC TAC TTA          1014
Pro Ala Gly Ala Pro Gln Arg His Ser Leu Ser Glu Ile Thr Tyr Leu
            315                 320                 325

GGG CAG CCA GAC ATC TCC ATC CTC CAG CCC TCC AAC GTG CCA CCT CCC          1062
Gly Gln Pro Asp Ile Ser Ile Leu Gln Pro Ser Asn Val Pro Pro Pro
            330                 335                 340

CAG ATC CTC TCC CCA CTG TCC TAT GCC CCA AAC GCT GCC CCT GAG GTC          1110
Gln Ile Leu Ser Pro Leu Ser Tyr Ala Pro Asn Ala Ala Pro Glu Val
345                 350                 355

GGG CCC CCA TCC TAT GCA CCT CAG GTG ACC CCC GAA GCT CAA TTC CCA          1158
Gly Pro Pro Ser Tyr Ala Pro Gln Val Thr Pro Glu Ala Gln Phe Pro
360                 365                 370                 375

TTC TAC GCC CCA CAG GCC ATC TCT AAG GTC CAG CCT TCC TCC TAT GCC          1206
Phe Tyr Ala Pro Gln Ala Ile Ser Lys Val Gln Pro Ser Ser Tyr Ala
                380                 385                 390

CCT CAA GCC ACT CCG GAC AGC TGG CCT CCC TCC TAT GGG GTA TGC ATG          1254
Pro Gln Ala Thr Pro Asp Ser Trp Pro Pro Ser Tyr Gly Val Cys Met
                395                 400                 405

GAA GGT TCT GGC AAA GAC TCC CCC ACT GGG ACA CTT TCT AGT CCT AAA          1302
Glu Gly Ser Gly Lys Asp Ser Pro Thr Gly Thr Leu Ser Ser Pro Lys
            410                 415                 420

CAC CTT AGG CCT AAA GGT CAG CTT CAG AAA GAG CCA CCA GCT GGA AGC          1350
```

```
His Leu Arg Pro Lys Gly Gln Leu Gln Lys Glu Pro Pro Ala Gly Ser
    425                 430                 435

TGC ATG TTA GGT GGC CTT TCT CTG CAG GAG GTG ACC TCC TTG GCT ATG      1398
Cys Met Leu Gly Gly Leu Ser Leu Gln Glu Val Thr Ser Leu Ala Met
440                 445                 450                 455

GAG GAA TCC CAA GAA GCA AAA TCA TTG CAC CAG CCC CTG GGG ATT TGC      1446
Glu Glu Ser Gln Glu Ala Lys Ser Leu His Gln Pro Leu Gly Ile Cys
                460                 465                 470

ACA GAC AGA ACA TCT GAC CCA AAT GTG CTA CAC AGT GGG GAG GAA GGG      1494
Thr Asp Arg Thr Ser Asp Pro Asn Val Leu His Ser Gly Glu Glu Gly
            475                 480                 485

ACA CCA CAG TAC CTA AAG GGC CAG CTC CCC CTC CTC TCC TCA GTC CAG      1542
Thr Pro Gln Tyr Leu Lys Gly Gln Leu Pro Leu Leu Ser Ser Val Gln
        490                 495                 500

ATC GAG GGC CAC CCC ATG TCC CTC CCT TTG CAA CCT CCT TCC GGT CCA      1590
Ile Glu Gly His Pro Met Ser Leu Pro Leu Gln Pro Pro Ser Gly Pro
    505                 510                 515

TGT TCC CCC TCG GAC CAA GGT CCA AGT CCC TGG GGC CTG CTG GAG TCC      1638
Cys Ser Pro Ser Asp Gln Gly Pro Ser Pro Trp Gly Leu Leu Glu Ser
520                 525                 530                 535

CTT GTG TGT CCC AAG GAT GAA GCC AAG AGC CCA GCC CCT GAG ACC TCA      1686
Leu Val Cys Pro Lys Asp Glu Ala Lys Ser Pro Ala Pro Glu Thr Ser
                540                 545                 550

GAC CTG GAG CAG CCC ACA GAA CTG GAT TCT CTT TTC AGA GGC CTG GCC      1734
Asp Leu Glu Gln Pro Thr Glu Leu Asp Ser Leu Phe Arg Gly Leu Ala
            555                 560                 565

CTG ACT GTG CAG TGG GAG TCC TGAGGGGAAT GGGAAAGGCT TGGTGCTTCC TCCC    1789
Leu Thr Val Gln Trp Glu Ser
        570

TGTCCCTACC CAGTGTCACA TCCTTGGCTG TCAATCCCAT GCCTGCCCAT GCCACACACT    1849

CTGCGATCTG GCCTCAGACG GGTGCCCTTG AGAGAAGCAG AGGGAGTGGC ATGCAGGGCC    1909

CCTGCCATGG GTGCGCTCCT CACCGGAACA AAGCAGCATG ATAAGGACTG CAGCGGGGGA    1969

GCTCTGGGGA GCAGCTTGTG TAGACAAGCG CGTGCTCGCT GAGCCCTGCA AGGCAGAAAT    2029

GACAGTGCAA GGAGGAAATG CAGGGAAACT CCCGAGGTCC AGAGCCCCAC CTCCTAACAC    2089

CATGGATTCA AAGTGCTCAG GGAATTTGCC TCTCCTTGCC CCATTCCTGG CCAGTTTCAC    2149

AATCTAGCTC GACAGAGCAT GAGGCCCCTG CCTCTTCTGT CATTGTTCAA AGGTGGGAAG    2209

AGAGCCTGGA AAAGAACCAG GCCTGGAAAA GAACCAGAAG GAGGCTGGGC AGAACCAGAA    2269

CAACCTGCAC TTCTGCCAAG GCCAGGGCCA GCAGGACGGC AGGACTCTAG GGAGGGGTGT    2329

GGCCTGCAGC TCATTCCCAG CCAGGGCAAC TGCCTGACGT TGCACGATTT CAGCTTCATT    2389

CCTCTGATAG AACAAAGCGA AATGCAGGTC CACCAGGGAG GGAGACACAC AAGCCTTTTC    2449

TGCAGGCAGG AGTTTCAGAC CCTATCCTGA GAATGGGGTT TGAAAGGAAG GTGAGGGCTG    2509

TGGCCCCTGG ACGGGTACAA TAACACACTG TACTGATGTC ACAACTTTGC AAGCTCTGCC    2569

TTGGGTTCAG CCCATCTGGG CTCAAATTCC AGCCTCACCA CTCACAAGCT GTGTGACTTC    2629

AAACAAATGA AATCAGTGCC CAGAACCTCG GTTTCCTCAT CTGTAATGTG GGGATCATAA    2689

CACCTACCTC ATGGAGTTGT GGTGAAGATG AAATGAAGTC ATGTCTTTAA AGTGCTTAAT    2749

AGTGCCTGGT ACATGGGCAG TGCCCAATAA ACGGTAGCTA TTTAAAAAAA AAAAAAAAA    2809

AAAAAAATAG CGGCCGCCTC GA                                             2831
```

(2) INFORMATION FOR SEQ ID NO:2:

(i) SEQUENCE CHARACTERISTICS:
        (A) LENGTH: 574 amino acids (B) TYPE: amino acid
(C) STRANDEDNESS: single
(D) TOPOLOGY: linear (ii) MOLECULE TYPE: protein (v) FRAGMENT TYPE: internal (xi) SEQUENCE DESCRIPTION: SEQ ID NO:2:

```
Met Arg Thr Leu Leu Thr Ile Leu Thr Val Gly Ser Leu Ala Ala His
  1               5                  10                  15

Ala Pro Glu Asp Pro Ser Asp Leu Leu Gln His Val Lys Phe Gln Ser
             20                  25                  30

Ser Asn Phe Glu Asn Ile Leu Thr Trp Asp Ser Gly Pro Glu Gly Thr
         35                  40                  45

Pro Asp Thr Val Tyr Ser Ile Glu Tyr Lys Thr Tyr Gly Glu Arg Asp
     50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
                100                 105                 110

Phe Ser Ser Leu Gln His Thr Thr Leu Lys Pro Pro Asp Val Thr Cys
            115                 120                 125

Ile Ser Lys Val Arg Ser Ile Gln Met Ile Val His Pro Thr Pro Thr
130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
                180                 185                 190

Pro Asp Thr Glu Phe Leu Gly Thr Ile Met Ile Cys Val Pro Thr Trp
            195                 200                 205

Ala Lys Glu Ser Ala Pro Tyr Met Cys Arg Val Lys Thr Leu Pro Asp
210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
            355                 360                 365

Thr Pro Glu Ala Gln Phe Pro Phe Tyr Ala Pro Gln Ala Ile Ser Lys
```

```
                     370              375              380
Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
                420                 425                 430

Lys Glu Pro Pro Ala Gly Ser Cys Met Leu Gly Gly Leu Ser Leu Gln
            435                 440                 445

Glu Val Thr Ser Leu Ala Met Glu Glu Ser Gln Glu Ala Lys Ser Leu
            450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
                500                 505                 510

Leu Gln Pro Pro Ser Gly Pro Cys Ser Pro Ser Asp Gln Gly Pro Ser
            515                 520                 525

Pro Trp Gly Leu Leu Glu Ser Leu Val Cys Pro Lys Asp Glu Ala Lys
530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570

(2) INFORMATION FOR SEQ ID NO:3:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GCAACTTTGA AAACATCCTG ACGTGGGACA GCGGGCCAGA GGGCACCCCA GACACGGTCT    60

ACAGCATCGA GTATAANACG TACGGAGAGA GGGACTGGGT GGCAAAGAAN GGCTGTCAGC   120

GGATCACCCG GAAGTCCTGC AACCTGACGG TGGAGACGGG CAACCTCACG GAGCTCTACT   180

ATGCCAGGGT CACCGCTGTC AGTGCGGGAG GCCGGTCANC CACCAAGATG ACTGACAGGT   240

TCAGCTCTCT GCAGCACACT ACCCTCAAGC CACCTGATGT GACCTGTATC TCCAAAGTGA   300

GATCGATTCN GATGATTGTT CATCCTACCC CCACGCCAAT CCGTGCAGGC GATG         354

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

AACATCCTGA CGTGGGACAG CGGGCCAGAG                                      30

(2) INFORMATION FOR SEQ ID NO:5:
```

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:5:

ACAGGTCACA TCAGGTGGCT TGAGGGTAGT                                    30

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GTCTGGGTTC GCTACTCGAG GCGGCCGCTA TTTTTTTTTT TTTTTTTT               48
```